United States Patent [19]

Vallee et al.

[11] Patent Number: 4,933,481

[45] Date of Patent: Jun. 12, 1990

[54] SYNTHESIS OF ORGANIC POLYSULPHIDES

[75] Inventors: Yannick Vallee, Caen; Yves Labat, Pau, both of France

[73] Assignee: Societe Nationale Elf Aquitaine (Production), Courbevoie, France

[21] Appl. No.: 385,404

[22] Filed: Jul. 27, 1989

[30] Foreign Application Priority Data

Aug. 23, 1988 [FR] France ............................ 88 11131

[51] Int. Cl.$^5$ .................................... C07C 148/00
[52] U.S. Cl. ................................................ 568/26
[58] Field of Search .......................................... 568/26

[56] References Cited

U.S. PATENT DOCUMENTS 3,392,201 7/1968 Warner ................................ 568/26

FOREIGN PATENT DOCUMENTS 2607496 6/1988 France .

OTHER PUBLICATIONS

E. Reid, Organic Chemistry of Bivalent Sulfur, vol. V, p. 429; vol. IV, pp. 141, 177, 178; Chemical Publishing Co. Inc. N.Y. (1960).

*Primary Examiner*—Mary E. Ceperley
*Attorney, Agent, or Firm*—Stevens, Davis, Miller & Mosher

[57] ABSTRACT

The invention relates to the production of organic polysulphides by the action of sulphur on a mercaptan.

According to the invention, the process is carried out in the presence of a thioxanthate formed separately or in situ by combination of carbon disulphide with a mercaptide.

12 Claims, No Drawings

SYNTHESIS OF ORGANIC POLYSULPHIDES

FIELD OF THE INVENTION

The invention relates to the production of organic polysulphides of the type $RS_nR$ where the two symbols R, which may be identical or different, each represent a hydrocarbon radical and n is a number ranging from 3 to 8, in particular from 4 to 6.

BACKGROUND OF THE INVENTION

These polysulphides, which have found diverse industrial applications, in particular as extreme pressure additives and as sulphidation agents for catalysts, are at present prepared industrially by the reaction of a mercaptan with liquid sulphur in the presence of a basic catalyst. In spite of a fairly high temperature (130°–140° C.), the reaction $$2RSH + (n-1)S \rightarrow RS_nR + H_2S$$

is often incomplete. The products obtained are turbid and contain mercaptan and free sulphur; they also contain a large proportion of heavy $S_6$, $S_7$, $S_8$ ... polysulphides which are unstable and steadily deposit sulphur.

The use, as catalyst, of the combination of a mercaptan with an alkene oxide and an alkali metal base (French Pat. No. 2,607,496, incorporated by reference) leads to a practically complete reaction, but noticeably increases production costs.

DETAILED DESCRIPTION OF THE INVENTION

It has now been found that the use of carbon disulphide allows the reaction to be carried out under mild conditions (10°–20° C.), while still retaining relatively short reaction times (a few hours), and clear yellow polysulphides to be obtained whose particularly high level of sulphur can attain the mean value of 5 atoms of sulphur per molecule of polysulphide. The level of mercaptan (SH) in the polysulphides thus obtained is zero (in any case less than 5 ppm), which indicates a complete reaction. In spite of their high level of sulphur, the products obtained contain few heavy polysulphides.

The combination of carbon disulphide with the mercaptide RSM formed by a mercaptan and a base leads to the formation of a thioxanthate

which has the role of catalyst in the production of the polysulphides.

The subject of the present invention is, therefore, a process for the preparation of organic polysulphides by the action of sulphur on a mercaptan, characterized in that the reaction is carried out in the presence of a thioxanthate formed by combination of carbon disulphide with a mercaptide.

The thioxanthate may be prepared separately by mixing approximately equimolar quantities of a mercaptan, a base and carbon disulphide in an inert organic solvent (for example methanol) and isolated by evaporation of the solvent. But, the best means of carrying out the process according to the invention consists in forming the thioxanthate in situ by stirring a mixture of mercaptan, base and carbon disulphide for a few minutes before introducing the sulphur necessary for the formation of the desired polysulphide.

The quantity of carbon disulphide to be used may vary within wide limits, provided that it is at least the molar equivalent of that of the base used. It is, however, advantageous to work with an excess of carbon disulphide with respect to the base, and, more particularly, using a volume of carbon disulphide which is between 0.5 and 1.5 times that of the mercaptan used.

Although it is preferred to use a well-defined mercaptan to obtain a symmetrical polysulphide, it would not be outside the scope of the present invention to use a mixture of mercaptans. In the starting mercaptan or mercaptans, the hydrocarbon radical may be aliphatic, cycloaliphatic or aromatic. However, alkyl mercaptans containing 2 to 15 carbon atoms and, more particularly, those with a tertiary alkyl radical are preferred.

The respective quantities of sulphur and mercaptan to be used depend on the polysulphide desired, that is to say on the mean number of sulphur atoms per molecule of polysulphide. In a general manner, the ratio: gramatoms of sulphur/moles of mercaptan may vary from 0.5 to 5. It is preferably between 1.5 and 2.5 to obtain polysulphides whose mean number of sulphur atoms per molecule is from 4 to 5.

The base used may be of an inorganic or organic nature. In particular, a metal hydroxide such as, for example, sodium or potassium hydroxide, or an amine, in particular a trialkylamine such as, for example, triethylamine, may be used. The base may be used in small quantities (for example from 0.01 to 2 mole per 100 moles of mercaptan), but also in large quantities (for example a molar equivalent with respect to the mercaptan).

In contrast to the previous methods which require heating above 100° C., leading to degradation of part of the polysulphides to disulphides, the reaction according to the invention does not necessitate heating and is, therefore, preferably carried out at ambient temperature (10°–20° C.). However, it would not be outside the scope of the present invention to operate at a lower or higher temperature, for example from 0° to 46° C. or even at a higher temperature if operating under pressure in a closed reactor.

The different polysulphides obtained according to the invention have a characteristic distribution. In fact, monosulphide is not observed, neither is disulphide and generally little trisulphide; and major product is tetrasulphide accompanied by a small amount of heavier sulphides.

The relatively low proportion of heavy sulphides (n>5), in spite of the fact that the number n is fairly high, allows the polysulphides obtained according to the invention to be stable, that is to say not to deposit sulphur on storage and to remain clear and yellow. The polysulphides obtained by other methods contain a large amount of heavy sulphides; they easily deposit sulphur and become turbid.

The following examples illustrate the invention without limiting it.

EXAMPLE 1

(a) Preparation of Triethylammonium Ethylthioxanthate 7.4 ml (0.1 mole) ethyl mercaptan and 13.8 ml (0.1 mole) triethylamine are stirred in 30 ml methanol for 15 minutes, then 6 ml (0.1 mole) carbon disulphide is added. An exothermic reaction takes place and the reaction mixture becomes slightly orange. The mixture is stirred for a further 3 hours, then the methanol is evaporated.

9 g of an orange paste are thus obtained whose NMR $^1$H and $^{13}$C spectra indicate it to be triethylammonium ethylthioxanthate

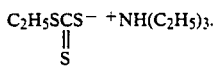

(c) Synthesis of Tert-Butyl Polysulphide

A mixture of 80 ml (0.71 mole) tert-butyl mercaptan, 80 ml carbon disulphide, 45.5 g (1.42 mole) sulphur and 0.1 g of the thioxanthate obtained above are stirred for 2 hours at ambient temperature. After evaporation of the carbon disulphide, 93 g of a clear yellow liquid are obtained which does not blacken acetate paper (absence of H$_2$S) and whose analysis indicates that the mean number of atoms of sulphur per molecule is 5, corresponding to the tert-butyl polysulphide of formula $(CH_3)_3CS_5C(CH_3)_3$.

EXAMPLE 2

Example 1-b is repeated, except that it is carried out in the absence of carbon disulphide and the mixture is stirred for 6 hours at ambient temperature. A polysulphide of mean formula $(CH_3)_3CS_{4.9}C(CH_3)_3$ is obtained in the form of a clear yellow liquid which does not blacken acetate paper.

EXAMPLE 3

80 ml (1.08 mole) ethyl mercaptan, 80 ml carbon disulphide and 0.4 ml (2.8 millimoles) triethylamine are stirred for half an hour at ambient temperature. 69.12 g (2.16 moles) of sulphur are then added. After stirring for 30 minutes, all the sulphur has disappeared. Stirring is continued for an hour and a half, then the carbon disulphide is evaporated.

111.5 g of a clear yellow oil which does not blacken acetate paper (no H$_2$S) are thus obtained. Its NMR $^1$H analysis shows that it consists of a mixture of ethyl polysulphides and its elementary analysis (S=73.8%) indicates that the mean number of sulphur atoms per molecule is 5.

EXAMPLE 4

A mixture of 80 ml (0.861 mole) isopropyl mercaptan, 80 ml carbon disulphide and 0.6 ml (4.3 millimoles) triethylamine are stirred for 15 minutes at ambient temperature. 56.6 g (1.768 mole) of solid sulphur are then added and stirring is continued for one hour.

The carbon disulphide and the triethylamine are then evaporated by bubbling nitrogen through the mixture and evaporation is finished using a rotary evaporator at 60° C. under 1600 Pa. Thus 103 g of a yellow liquid which does not blacken acetate paper and whose residual mercaptan level is less than 5 ppm are obtained. Microanalysis indicates a sulphur content of 63.3%, which corresponds to the mean formula:

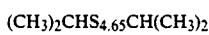

Yield: 97%.

EXAMPLE 5

This is carried out in the same way as Example 4 using 80 ml (0.71 mole) tert-butyl mercaptan, 80 ml carbon disulphide, 0.8 ml (5.7 millimoles) triethylamine and 45.5 g (1.42 mole) sulphur. 92.3 g of a clear yellow liquid which does not blacken acetate paper are obtained. Analysis of its NMR $^1$H spectrum indicates the following molar distribution:

disulphide: 0
trisulphide: 1%
tetrasulphide: 48%
pentasulphide: 21%
hexasulphide: 12%
hepta- and octasulphide: 18%

The mean number of sulphur atoms per molecule is 4.9 and the yield is 96%.

EXAMPLE 6

If Example 5 is repeated, but with only 34.3 g (1.065 mole) sulphur, 76.5 g of a clear yellow polysulphide which does not blacken acetate paper and whose level of residual mercaptan is less than 5 ppm are obtained.

Microanalysis (S=54.3%) indicates a mean number of 4.3 atoms of sulphur per molecule and NMR $^1$H analysis shows the following molar distribution: $S_3=1\%$, $S_4=69\%$, $S_5=19\%$, $S_6=7\%$, $S_7-S_8=4\%$.

EXAMPLE 7

This is carried out in the same way as Example 4 with 80 ml (0.465 mole) tert-octyl mercaptan, 80 ml carbon disulphide, 0.4 ml triethylamine and 29.8 g (0.93 mole) sulphur.

79 g of a clear yellow polysulphide which does not blacken acetate paper and whose level of residual mercaptan is below 5 ppm are obtained. Microanalysis indicates a sulphur content of 41.5%, which corresponds to a mean number of 5 atoms of sulphur per molecule.

Yield: 88%.

EXAMPLE 8

This is carried out in the same way as Example 4 with 100 ml (0.425 mole) tert-dodecyl mercaptan, 100 ml carbon disulphide, 0.5 ml triethylamine and 27.2 g (0.85 mole) sulphur. Because the sulphur dissolves slowly, stirring is maintained for 4 hours before bubbling nitrogen through the mixture. The evaporation at 60° C. under 1600 Pa must be carried out for 5 hours so that the clear yellow liquid only blackens acetate paper slightly.

The level of residual mercaptan is less than 5 ppm. Microanalysis indicates a sulphur content of 31.7%, corresponding to a mean number of 4.9 atoms of sulphur per molecule.

EXAMPLE 9 (COMPARATIVE TO EXAMPLE 6)

A mixture of 80 ml tert-butyl mercaptan, 0.8 ml triethylamine and 34.3 g sulphur is stirred at ambient temperature, in the absence of carbon disulphide.

After 16 hours of stirring, the solid sulphur which has not reacted is filtered off. A slightly orange, turbid polysulphide is obtained, the NMR $^1$H analysis of which indicates the presence of trisulphide and gives the following molar distribution: $S_3=16\%$, $S_4=56\%$, $S_5=14\%$, $S_6=8\%$, $S_7-S_8=6\%$.

The mean number of sulphur atoms is 4 in place of the 4.3 of example 6.

EXAMPLE 10

56 ml (0.5 mole) tert-butyl mercaptan and 40 ml carbon disulphide are added to a solution of 20 g (0.5 mole) of sodium hydroxide in 200 ml methanol. The mixture is stirred for 30 minutes, then 32 g sulphur are added and stirring is continued for 16 hours.

The carbon disulphide is then evaporated by air stripping, then the precipitate ($Na_2S$) is filtered off and the methanol evaporated with a rotary evaporator. 46 g of a polysulphide, whose mean number of sulphur atoms per molecule is 4, are thus obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the preparation of organic polysulphides by the action of sulphur on a mercaptan, comprising carrying out the reaction in the presence of a thioxanthate formed by combination of carbon disulphide and a mercaptide.

2. The process according to claim 1, wherein the operation is carried out at a temperature ranging from 0° to 46° C.

3. The process according to claim 2, wherein the temperature is ambient temperature.

4. The process according to claim 1, wherein per mole of mercaptan, from 0.5 to 5 gram-atoms of sulphur are used.

5. The process according to claim 4, wherein per mole of mercaptan from 1.5 to 2.5 gram-atoms of sulphur are used.

6. The process according to claim 1, wherein the mercaptan is an alkyl mercaptan.

7. The process according to claim 6, wherein the mercaptan is a tertiary alkyl mercaptan.

8. The process according to claim 1, wherein sulphur is introduced into a mixture of a mercaptan, a base and carbon disulphide.

9. The process according to claim 8, wherein a volume of carbon disulphide is used ranging from 0.5 to 1.5 times that of the mercaptan used.

10. The process according to claim 8, wherein the base is a metal hydroxide or an amine.

11. The process according to claim 10, wherein the amine is a trialkylamine.

12. The process according to claim 8, wherein at least 0.1 millimole of base is used per mole of mercaptan.

* * * * *